United States Patent
Suominen

(10) Patent No.: US 7,160,713 B2
(45) Date of Patent: Jan. 9, 2007

(54) METHOD AND APPARATUS FOR OXIDIZING ORGANIC MATTER

(76) Inventor: Hannu L. Suominen, 7801 Kingsview L.N., Maple Grove, MN (US) 55311

( * ) Notice: Subject to any disclaimer, the term of this patent is extended or adjusted under 35 U.S.C. 154(b) by 660 days.

(21) Appl. No.: 10/286,823

(22) Filed: Nov. 4, 2002

(65) Prior Publication Data

US 2004/0063193 A1 Apr. 1, 2004

(30) Foreign Application Priority Data

Sep. 27, 2002 (FI) .............................. 20021727

(51) Int. Cl.
*C05F 17/00* (2006.01)
*C05F 17/02* (2006.01)

(52) U.S. Cl. ............... 435/262; 435/290.4; 435/299.1; 71/9; 210/609

(58) Field of Classification Search ............ None
See application file for complete search history.

(56) References Cited

U.S. PATENT DOCUMENTS

| 4,062,770 A | 12/1977 | Kneer |
| 5,234,596 A | 8/1993 | Greeb |
| 6,254,779 B1 * | 7/2001 | Jeffery et al. ............... 210/620 |
| 2002/0096459 A1 | 7/2002 | Suzuki et al. |

FOREIGN PATENT DOCUMENTS

| EP | 0566256 A1 | 10/1993 |
| FI | 88609 | 2/1993 |
| JP | 06071282 A * | 3/1994 |
| WO | WO 9116282 A1 * | 10/1991 |

* cited by examiner

*Primary Examiner*—William H. Beisner
(74) *Attorney, Agent, or Firm*—Connolly, Bove, Lodge & Hutz, LLP

(57) ABSTRACT

Method and apparatus for biologically oxidizing organic matter. Finely powdered organic matter is suplied into the top end of an upright, high reaction vessel (1). The vessel (1) has been filled up substantially completely by small balls, on the surfaces of which the matter to be oxidized is present in thin layers. By means of a conveyor (6) outside the vessel, the balls are transferred uppwards, whereby the balls in the reaction vessel (1) flow downwrds. Oxidizing air is blown uppwrds against the flow of balls, whereby in the upper section of the vessel, drying takes place in the first instance and then is formed an oxidizing zone automatically by microbial activity in a section, wherein the best oxidizing conditions are prevailing. Exhaust air is cleaned by means of ionic cleaners (14) and singlet oxygen generators (27) and oxidized matter is recovered from the bottom end of the reaction vessel.

12 Claims, 1 Drawing Sheet

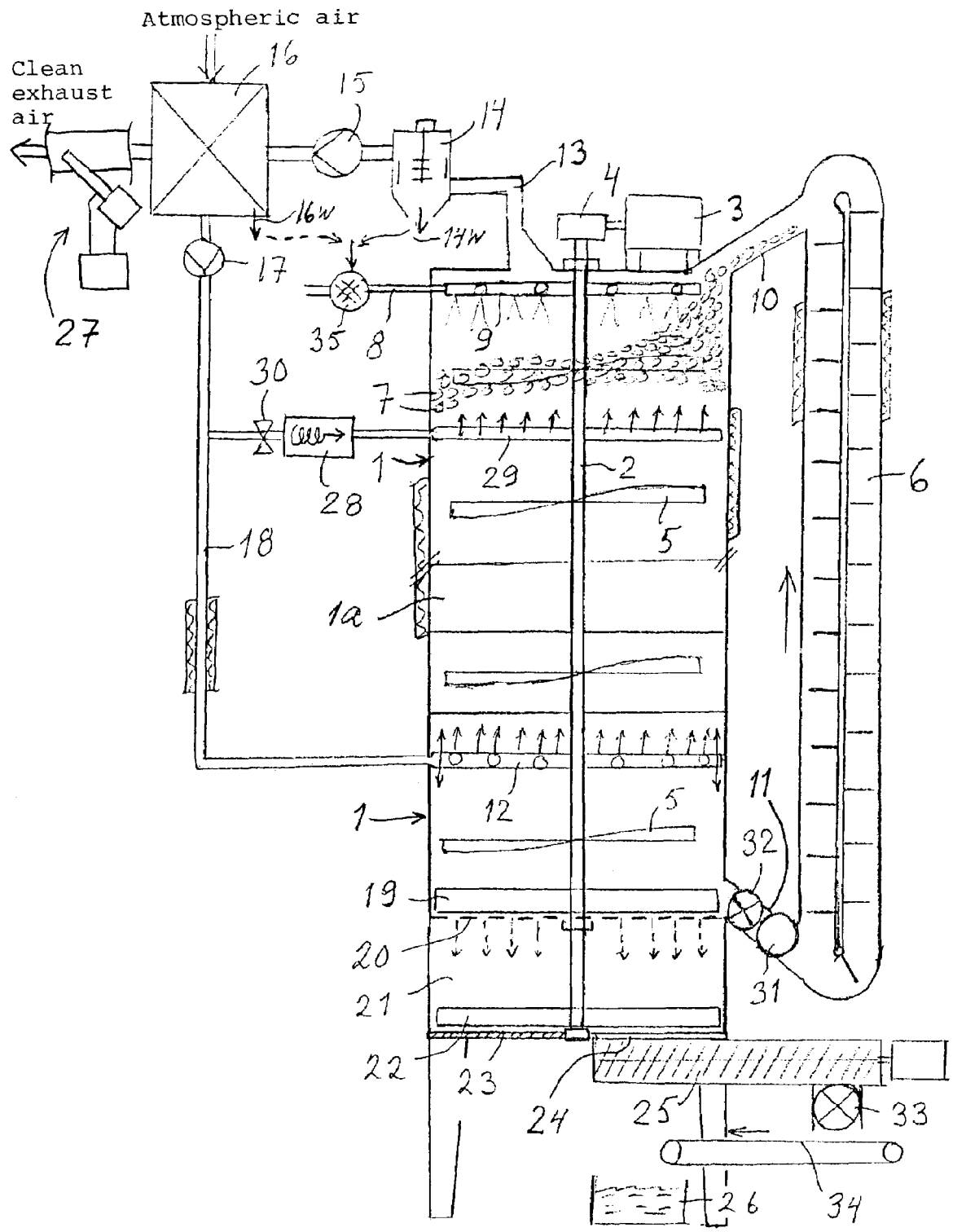

METHOD AND APPARATUS FOR OXIDIZING ORGANIC MATTER

The invention relates to a method for biologically oxidizing organic matter. The method comprises oxidizing organic matter in a reaction vessel, which is supplied with air regulated in terms of heat and humidity and from which is discharged a hot moist gas. For enhanced oxidation, the organic matter is provided with a recyclable oxidizing surface. The organic matter comprises typically fluidized finely powdered waste.

The invention relates also to an apparatus for oxidizing organic matter while the organic matter is in the state of finely powdered waste, said apparatus comprising a reaction vessel, devices for supplying matter to be oxidized into the reaction vessel, devices for circulating an oxidizing surface in the reaction vessel, devices for separating oxidized matter from the circulated oxidizing surface and from biologically unoxidized matter, devices for supplying the reaction vessel with air regulated in terms of heat and humidity, devices for drawing a hot moist exhaust gas from the reaction vessel, devices for scrubbing the exhaust gas, and a heat recovery unit for the transmission of heat from the exhaust gas to the inlet air.

Organic matter is supplied at the top end of a reaction vessel and a valuable final product, useful e.g. as a soil conditioner, is obtained from the bottom end of the reaction vessel. In the reaction vessel, high-temperature micro-organisms use the organic matter for nutrition. When growing and multiplying, the microbes demand nutrition and enormous amounts of oxygen. At the same time, they produce thermal energy, water, carbon dioxide, and useful biomass.

When the organic matter has a dry content (ka) which is low, e.g. in organic sludges ka<20%, it will be problematic to provide oxidation sufficiently effective for such a microbial activity which is required for a total oxidation of the organic matter. This problem has been addressed by adding various builders in the sludge mass, such as wood chips, peat, etc., but the constitution and composition of such prior known builders do not provide an optimal oxidation performance.

The invention concerns a method and apparatus capable of maximizing the oxidation performance of a biological oxidation process, i.e. the oxygen supply of microbes, so as to speed up the entire oxidation process, to oxidize all of the organic matter, and to provide a substantial increase in production capacity more economically than in the prior known methods.

BREIF DESCRIPTION OF THE FIGURE

One embodiment of the invention will now be described in more detail with reference to the accompanying drawing, showing an apparatus of the invention in a schematic vertical section.

A thermally insulated reaction vessel 1 comprises an upright cylinder, having a height which exceeds its diameter. In the middle of the cylinder 1 is a rotatable shaft 2, driven by a motor 3 at a variable speed through the intermediary of a reduction gear 4. A manifold or distributor plate 9, consisting of pipe rings and radial tubular members interconnecting the same, disperses organic matter evenly across the vessel 1 in its top end. The organic matter is delivered by means of a pipe 8 into the manifold or plate 9. The organic matter may comprise e.g. sludge from a sewage treatment plant, liquid porcine manure or other agricultural liquid manure or other organic waste. The dry content of organic matter to be treated with the apparatus is typically 1–30%, whereby it is generally in a fluid state when ka<15%. When ka>15%, it may be beneficial to elutriate the matter in water prior to oxidation. Dry waste can also be milled to a finely powdered form and elutriated in water for bringing the waste to a fluid state and for facilitating separation of the unoxidized portion from the oxidized product and the oxidizing surface.

The vessel 1 is filled with substantially round bodies, e.g. spheres 7, of an essentially totally unoxidizable material, having a diameter within the range of 1–5 cm, most preferably about 2–3 cm, and having their surface treated in such a way that the organic matter is highly adhesive to the spherical surface. If the organic matter is excessively dry, it is possible to add water therein through a mixer 35 for making it adhere to the surface of the spheres 7 in the form of a thin layer. It is an objective that the spherical surface be provided with such a thin layer of oxidizable matter that the oxygen obtained from regulated air penetrates the layer of material on the spherical surface. The layer of material has a thickness which is typically less than 2 mm.

The shaft 2 is fitted with vane-like stirring elements 5, extending towards a wall of the reaction vessel 1. Spheres are carried by a conveyor 6 from the bottom to the top of the reaction vessel 1. A result of this is, of course, that within the vessel 1 is a flow of spheres which is directed downwards. As the spheres are generally lighter than the matter to be oxidized, having e.g. a specific weight of about 0,5 kg/dm$^3$ or less, the spheres, which are coated with a substance having a density higher than that of the spheres, strive to descend faster than cleaner spheres, with the result that substantially all the spheres receive a coating from the matter to be oxidized. The spheres 7 are returned by way of a cover of the vessel 1 and the matter to be oxidized is passed therebelow for precluding the formation of aerosols.

Regulated oxidation air is blown into the reaction vessel 1, generally from below its middle section. Therefor, the reaction vessel 1 has its inner wall fitted with a pipe frame 12, including orifices and having air supplied therein by means of a pump 17 through a duct 18, typically from a heat recovery unit 16. The pipe frame 12 comprises e.g. annular and radial pipes. The pipe frame 12 has its vertical position preferably adjustable. The adjustment can be implemented by a vertical adjustment of hangers placed within the vessel 1.

The reaction vessel 1 can have its height adjustable by adding or removing cylindrical blocks 1a, which can be placed on top of each other for assembling the reaction vessel like a lego tower.

The discharge of air from the bottom end of the vessel is precluded, e.g. in such a way that a receiving space 21 for oxidized matter has a bottom 23, which is otherwise solid except for a gap 24 connecting the space 21 with a conveyor 25 which can be connected, if necessary, by way of a shut-off feeder 33 with another conveyor 34 for delivering a finished product into a container 26. Thus, the air is forced to flow in the reaction vessel 1 up towards the top end of the reaction vessel. The reaction vessel has its top end provided with an exhaust fan 15 for drawing out the air fed inside the reaction vessel and for guiding it out through an air cleaner 14 and the heat recovery unit 16 and an air cleaner 27. The spheres 7 constitute a dense homogeneous system of flow channels distributed all over the reaction vessel 1, having in association therewith a large surface area of the substance to be oxidized. At the mid-height section of the reaction vessel is established a so-called oxidizing zone, wherein moisture and oxygen conditions, as well as temperature, are appropriate for microbial activity. The oxidizing microbial activity will be particularly effective as the entire amount of air proceeds continuously through the entire oxidizing zone and the material to be oxidized. The air heated in biological oxidation and the dry hot air supplied, if necessary, into the vessel's top section are capable of drying the material in the vessel's top section, such that it has been appropriately dried by the time it reaches the oxidizing zone, which self-establishes itself always in a given region between an air supply point 12 and the reaction vessel's top end. The residence or dwell time of a material to be oxidized is regulated by means of the sphere conveyor 6 and the reaction vessel's top end is supplied with just enough material to provide a suitable material layer on the spherical surface. Regulation parameters include also a flow rate of air, its temperature and humidity.

Reference numeral 14 designates a discharge air cleaner. In practice, the discharge or exhaust air can be cleaned most preferably by means of ionic cleaners 14 and singlet oxygen generators 27 (patent application FI 20020304). The discharge air can be cleaned with ionic cleaners which are known per se, e.g. from publications EP-1178860 and EP-1165241. Operation of the ionic cleaner or ionizing particle separator 14 is based on charging the particles present in the air flowing through a void separator chamber, and on collecting the charged particles by means of an electric field onto grounded or live collecting surfaces, from which the particles are flushed with water and the flushing water is most preferably recycled back to the oxidizing process and discharged through a heat exchanger 16 as condensation water. The number of ionic cleaners 14 is typically two or more (just 1 is shown), and the air flow therebetween travels in a multitude of ionic blowpipes, which are fitted with the singlet oxygen generator 27. The Applicant's patent application FI 20020304 discloses an example of the suitable ionic cleaner 14 and the singlet oxygen generator 27. In the present case, the singlet oxygen generator 27 is positioned downstream of the heat exchanger 16, which may also be provided with a separate condenser for the condensation of water vapour. The singlet oxygen generator 27 comprises an electrically conductive electrode inside a glass tube, and outside the glass tube is a spiral electrode inside a dielectric. Between the ends of these electrodes is coupled a high-frequency source of high voltage. The tube and the electrodes are housed in a jacket tube, through which air is blown by means of a fan, said air entraining singlet oxygen which is produced by a corona effect breaking up oxygen molecules of the flowing air, said corona effect being created by the spiral electrode.

The fan 15 expels the refined gases through the heat exchanger 16, and the fan 17 delivers dry clean atmospheric air, which has been heated in a regulated fashion in the heat exchanger 16, through the duct 18 into the reaction vessel 1 and/or through a separate heater 28 and a distributor 29 into the top section of the reaction vessel 1. If blow drying for the top section is not needed, it can be shut off by means of a control valve 30.

In major facilities, it is preferred that a common air treatment unit be built for a plurality of reaction vessels 1.

The reaction vessel 1 is provided with a perforated floor 20, which has a hole size substantially smaller than the diameter of the spheres 7 and below which is the receiving space 21 for oxidized matter. A scraper blade 19 driven by the shaft 2 scrapes the perforated floor 20, pushes the oxidized powdered product through the holes, and prevents blocking of the floor holes and simultaneously advances spheres by way of a shut-off feeder 32 onto the conveyor 6.

Thus, the perforated floor 20 constitutes a screen, above which occurs effective mixing by means of the scraper 19 and the stirring vanes 5, in order to effect stripping of the oxidized matter from the spheres 7. Hence, between the floor 20 and the blowpipe system 12 is established a stripping zone, in which the stirring vanes 5 have their blades arranged more densely than elsewhere above the pipe system 12.

The spheres 7 are preferably made of a homogeneous material, whereby, while wearing, said spheres develop continuously the same effective gripping surface which is highly adhesive for the material. Although the bodies 7 have preferably the shape of a sphere and in this context are referred to as "spheres", it should be understood that these may comprise bodies of other shapes or materials with a high surface area to volume ratio.

The invention is not limited to the above-described embodiment as its structural details may involve a multitude of variations. For example, the sphere conveyor 6 can be built inside the vessel 1 as a lifting screw. The stirring elements 5 are not necessarily mobile but, instead, may comprise stationary guides.

The reaction vessel 1 can be supplied not only with sludge, but also with dry waste, as long as it has been comminuted beforehand. Humidity control is carried out by condensation water 16w, and by flushing water 14w for the ionic fans 14, which is always recycled back to circulation.

Waste materials can be pre-aerated and, if necessary, sludges can be adjusted to such an acidic pH that ammonia does not evaporate and cause losses of N in fertilizer production.

Even debris-containing biowaste can be oxidized by setting a screen 31 upstream of the sphere conveyor 6 for the removal of debris. Thus, the apparatus is applicable as a general purpose oxidizer for all sorts of organic matter. The apparatus can be constructed to be very compact or very large.

The function of the shut-off feeders 32 and 33 is to preclude the outflow of air from the reaction vessel 1 anywhere else except from the top by means of the exhaust fan 15.

The reaction vessel 1 and all pipes, conveyors and other equipment are thermally insulated.

The inventioned claimed is:

1. A method for biologically oxidizing organic matter waste, said method comprising:
    directing the organic waste to a top end of a reaction vessel (1), wherein the reaction vessel is substantially filled with biologically unoxidizable spheres (7), upon which the surfaces of the spheres the organic matter to be oxidized is present as thin layers,
    directing oxidizing air regulated in terms of heat and humidity to the reaction vessel below an oxidizing zone of the reaction vessel, and above a perforated floor, said floor precludes the spheres from falling into a waste receiving area disposed below the reaction vessel, but allows the treated waste to pass into the receiving area;
    discharging exhaust gas from the top end of the reaction vessel and scrubbing the exhaust gas,
    discharging substantially dry oxidized matter from the receiving area of the reaction vessel, and
    transporting the spheres (7) from the bottom end to the top end of the reaction vessel (1) to control the rate at which the spheres gravitate downward through the reaction vessel.

2. A method as set forth in claim 1, further comprising scrubbing the exhaust gas with an ionic cleaner (14), a singlet oxygen generator (27) or both the ionic cleaner and the oxygen generator.

3. The method of claim 1, further comprising transferring dry treated waste that falls to the perforated floor into the receiving area with a scraper positioned above the perforated floor to facilitate the transfer of treated waste from the reaction vessel into the receiving area.

4. The method of claim 1, further comprising stripping the dry treated organic waste from the surface of the spheres in a stripping zone disposed between the perforated floor and the air injection manifold, the stripping zone comprising a relative dense concentration of stirring elements.

5. A method for oxidizing powdered organic matter, the method comprising:

providing a reacting vessel with a height dimension that is greater than any base dimension, wherein the reaction vessel is substantially filled with spheres upon which the surface of the spheres becomes coated with a thin layer of the organic matter that is introduced into the reaction vessel with a waste input manifold;

injecting air with an air injection manifold to the reaction vessel, said injection manifold disposed below an oxidizing zone and above a perforated floor, said floor precludes the spheres from falling into a waste receiving area disposed below the reaction vessel, but allows the treated waste to pass into the receiving area;

removing exhaust gas from the reaction vessel and treating the exhaust gas;

moving the spheres in the reaction vessel with stirring elements as the spheres gravitate downward through the reaction vessel; and transporting the spheres from the bottom to the top of the reaction vessel with a conveying element.

6. The method of claim 5, wherein the reaction vessel is cylindrically shaped and the base dimension is its diameter.

7. The method of claim 5, further comprising transferring dry treated waste that falls to the perforated floor into the receiving area with a scraper positioned above the perforated floor to facilitate the transfer of treated waste from the reaction vessel into the receiving area.

8. The method of claim 5, wherein the injected air is introduced below the oxidation zone, said oxidizing zone essentially located at the mid-height section of the reaction vessel, where moisture and oxygen levels and temperature are appropriate for promoting microbial activity.

9. The method of claim 5, further comprising a heat exchanger for transferring heat from the exhaust gas to the supply air prior to introducing the air to the reaction vessel.

10. The method of claim 5, wherein the treating of the exhaust gas comprises scrubbing the exhaust gas with a scrubbing unit selected from an ionic cleaner, a singlet oxygen generator or both the ionic cleaner and the oxygen generator.

11. The method of claim 5, further comprising stripping the dry treated organic waste from the surface of the spheres in a stripping zone disposed between the perforated floor and the air injection manifold, the stripping zone comprising a relative dense concentration of the stirring elements.

12. The method of claim 5, further comprising controlling the moisture of the injected air with a humidity control unit.

\* \* \* \* \*